United States Patent [19]

Levy et al.

[11] Patent Number: 5,580,769

[45] Date of Patent: *Dec. 3, 1996

[54] CD8+ CELL ANTIVIRAL FACTOR

[75] Inventors: Jay A. Levy; Carl E. Mackewicz, both of San Francisco, Calif.

[73] Assignee: The Regents of The University of California, Oakland, Calif.

[ * ] Notice: The portion of the term of this patent subsequent to Sep. 17, 2013, has been disclaimed.

[21] Appl. No.: 307,179

[22] Filed: Sep. 16, 1994

Related U.S. Application Data

[63] Continuation-in-part of Ser. No. 122,221, filed as PCT/US92/09302, Oct. 30, 1992, which is a continuation-in-part of Ser. No. 786,114, Nov. 1, 1991, abandoned.

[51] Int. Cl.$^6$ .......................... C12N 15/00; G01N 33/53; C07K 1/00; A61K 39/00

[52] U.S. Cl. .................. 435/172.3; 435/7.2; 435/7.24; 424/184.1; 424/577; 530/350

[58] Field of Search .............................. 435/172.3, 7.2, 435/7.24; 424/184.1, 577; 530/350

[56] References Cited

U.S. PATENT DOCUMENTS 4,818,683  4/1989  Morel et al. .

FOREIGN PATENT DOCUMENTS

WO94/23058  10/1994  WIPO .

OTHER PUBLICATIONS

Brichmann et al., "CD8+ T Cells Inhibit HIV Replication in Naturally Infected CD 4 +T Cells: Evidence for a Soluble Inhibitor," *J. Immunol.* (1990) 144:2961–2966.

Mackewicz et al., "CD8+ Cell Anti–HIV Activity Correlates with the Clinical State of the Infected Individual," *J. Clin. Invest.* (1991) 87:1462–1466.

Walker et al., "CD8+ Lymphocytes Can Control HIV Infection in Vitro by Suppressing Virus Replication," *Science* (1986) 234:1563–1566.

Walker et al., "A Diffusable Lymphokine Produced by CD8+ T Lymphocytes Suppresses HIV Replication," *Immunology* (1989) 66:628–630.

Castro et al., "Suppression of Human Immunodeficiency Virus Replication by CD8+ Cells from Infected and Uninfected Chimpanzees," *Cellular Immunology* (1991) 132:246–255.

Laurence, et al, 1990, "A soluble inhibitor of . . . " Cellular Immunology 128:337–352.

*Primary Examiner*—Lynette F. Smith
*Attorney, Agent, or Firm*—Karl Bozicevic; Fish & Richardson P.C.

[57] ABSTRACT

A protein secreted by peripheral blood mononuclear specifically from CD8+ lymphocytes is purified and characterized here and designated CD8+ cell antiviral factor (CAF). The CAF is lipid free and has been found to inhibit the replication of retroviruses and in particular to inhibit the replication of HIV-1, HIV-2, and SIV. CAF can be used to inhibit viral RNA transcription which inhibits viral replication. Accordingly, CAF can be used to treat patients infected with retroviruses. The CAF can also generate antibodies which can be used to create assay devices for detecting CAF in a body fluid and on the surface of CD8+ cells to determine the condition of an HIV infected individual.

9 Claims, No Drawings

CD8+ CELL ANTIVIRAL FACTOR

CROSS-REFERENCES

This application is a continuation-in-part of our earlier filed application Ser. No. 08/122,221 filed Sep. 17, 1993 which is a continuation-in-part of PCT/US92/09302 filed Oct. 30, 1992 which is a continuation-in-part of Ser. No. 07/786 114 filed Nov. 1, 1991, now abandoned, to which applications we claim priority under 35 USC §120 and which applications are incorporated herein by reference.

FIELD OF THE INVENTION

This invention relates generally to anti-viral compounds, methods of using such antibodies and assays obtained therefrom. More particularly, the invention relates to a purified CD8+ cellular protein which inhibits the replication of retroviruses and specifically inhibits the replication of human immunodeficiency virus (HIV).

BACKGROUND OF THE INVENTION

Considerable efforts are being made toward finding a compound which will effectively inhibit the replication of retroviruses and in particular to inhibit HIV replication. In order to be useful in treating an individual infected with HIV the compound would be required to inhibit HIV replication while not being fatally toxic to normal cells.

The present inventors noted the relationship between CD8+ cell anti-HIV activity and the clinical condition of an individual infected with HIV. Mackewicz, C.E. et al., CD8+ cell anti-HIV activity correlates with the clinical state of the infected individual, *J. Clin. Invest.* 87, 1462–1466, 1991. With this relationship in mind efforts were made to extract from CD8+ cells a component which is capable of inhibiting HIV replication. Others have studied CD8+ cells and the effects of such cells on vital replications. For example see Brinchmann et al., "CD8+ T Cells Inhibit HIV Replication in Naturally Infected CD4+ T Cells," *Journal of Immunology* (1990) 144:2961–2966; Walker et al., "CD8+ Lymphocytes Can Control HIV Infection In Vitro by Suppressing Virus Replication," *Science* (1986) 234:1563–1566; Walker et al., "A diffusible lymphokine produced by CD8+ T lymphocytes suppresses HIV replication," *Immunology* (1989) 66:628–630.

Brinchmann et al. teach placing the CD8+ cells in proximity to cells infected with HIV. Based thereon, Brinchmann et al. speculated that some factor or factors are excreted from the CD8+ cells which inhibits HIV proliferation. There is no disclosure or attempt made with respect to: (1) isolating what that factor(s) might be; (2) determining if a single factor was responsible as opposed to a number of different compounds being excreted by the CD8+ cells; or (3) determining if such factor(s) are different from factors known at the time.

The two Walker et al. publications do not isolate and characterize such a factor and do not indicate that a specific factor, different from other known factors, is responsible for inhibiting HIV replication.

Although others have noted a relationship between CD8+ cells and HIV replication, they have not isolated any single protein extractable from the cells which could be shown as the basis for antiviral activity. The present inventors have isolated and characterized such a protein.

SUMMARY OF THE INVENTION

A protein secreted by peripheral blood CD8+ lymphocytes is purified and characterized here and designated CD8+ cell antiviral factor (CAF). Specifically, CAF can be precipitated from a CD8+ cell supernatant by 53% ammonium sulfate. The CAF is lipid free, has a molecular weight of less than 30,000 and has been found to inhibit the replication of retroviruses and in particular to inhibit the replication of HIV-1, HIV-2, and SIV, although CAF does not inactivate HIV and does not affect expression of CD4+ cell activation markers and does not block CD4+ cell replication. CAF can be used to inhibit viral RNA transcription which inhibits the production of infectious viruses. Accordingly, CAF can be used to treat patients infected with retroviruses.

An important object of the invention is to provide substantially pure CAF which is capable of inhibiting the replication of retroviruses and in particular HIV.

Another object of the invention is to provide pharmaceutical formulations containing CAF.

Yet another object is to provide antibodies (polyclonal and monoclonal) generated by CAF and assays and methods using such antibodies.

A specific object is to provide an ELISA assay using CAF antibodies which assay can be used to detect the presence and amount of CAF in a body fluid.

Still another object is to provide a purified protein which can be used as a chemical reagent to inhibit viral RNA transcription.

An advantage of the CAF is that it does not affect expression of CD4+ cell activation markers or their proliferation while blocking retroviral replication.

Features of the CAF are that it is released from CD8+ cells, inactivated when exposed to a pH of 10–12 and not inactivated when exposed to a pH in the range of 2–8, resistant to heat and trypsin and immunologically distinct from a range of known cytokines.

These and other objects, advantages and features of the present invention will become apparent to those persons skilled in the art upon reading the details describing CD8+ cell antiviral factor as well as the use of the factor and its antibodies as more fully set forth below, reference being made to the specific examples and formulations forming a part hereof.

DETAILED DESCRIPTION OF PREFERRED EMBODIMENTS OF THE INVENTION

Before the present CD8+ antiviral factor and methods for using such are described, it is to be understood that this invention is not limited to the particular methods described as such may, of course, vary. It is also to be understood that the terminology used herein is for the purpose of describing particular embodiments only, and is not intended to be limiting, as the scope of the present invention will be limited only by the appended claims.

It must be noted that, as used in this specification and the appended claims, the singular forms "a", "an", and "the" include plural referents unless the context clearly dictates otherwise. Thus, for example, reference to "a pharmaceutically acceptable carrier" includes mixtures of such carriers, reference to "an antiviral factor" includes more than one molecule of such and reference to "the assay method" includes different types of assays and methods of using same and so forth.

Unless defined otherwise, all technical and scientific terms used herein have the same meaning as is commonly understood by one of ordinary skill in the art to which this invention belongs. Although any methods and materials similar or equivalent to those described herein may be useful in the practice or testing of the present invention, preferred methods and materials are described below. All publications mentioned herein are incorporated herein by reference. Further, specific terminology of particular importance to the description of the present invention is defined below.

The terms "CD8$^+$ cell antiviral factor" and "CAF" are used interchangeably herein to refer to a protein which is obtained from peripheral blood CD8$^+$ lymphocytes. Specifically, CAF can be precipitated from a CD8$^+$ cell supernatant by 53% ammonium sulfate and has been determined as having the following characteristics:

a. released from activated CD8$^+$ cells;

b. biologically inactivated when exposed to a pH in a range of 10–12 while maintaining biological activity when exposed to a pH in the range of 2–8;

c. resistant to heat of 100°C. for 30 minutes to the extent that about 60% of its activity is maintained and when maintained at 100°C. for 10 minutes activity of up to 90% is maintained;

d. insensitive to trypsin activity at 37°C. for one hour;

e. does not affect CD4$^+$ cell activation or proliferation;

f. blocks viral replication by inhibiting viral RNA transcription;

g. function not inhibited by antibodies specific for IFNα, IFNβ, IFNγ, TNFα, TNFβ, TGFβ, IL-4 or IL-6;

h. is not a cytokine selected from the group consisting of IL-1, IL-2, IL-3, IL-4, IL-5, IL-6, IL-7, IL-8, IL-9, IL-10, IL-12, G-CSF, GM-CSF, TNFα, TNFβ, IFNα, IFNβ, IFNγ, and TGFβ;

i. activity is maintained after being subjected to freezing and thawing;

j. sensitive to staph V8 protease but not to protease type XIA (proteinase K);

k. does not induce 2'–5'-A synthetase in CD4+ lymphocytes and is, accordingly, different from interferon;

l. precipitated from CD8$^+$ cell supernatant by 53% ammonium sulfate;

m. lipid free;

n. an average molecular weight of less than 30,000 in that it passes through 30 Kd MW cutoff CENTRICON filters. The size of CAF is estimated at 30,000 daltons based on Amicon filter exclusion techniques. Recently, using leupeptin column purification, the protein appears to be as large as 62,000 daltons. This latter finding may reflect the inability of Amicon filtering to give a discrete molecular weight or the presence in column purification of dimer of CAF;

o. inactivated by leupeptin but not inactivated by benzamidine;

p. binds to a carboxy methylcellulose ion exchange resin at a pH of about 6.0.; and q. reduces luciferase expression in IG5 cells infected with HIV.

Human peripheral blood CD8$^+$ lymphocytes which produce the CAF have been deposited as ATCC Designation CRL 11453 on Sep. 16, 1993. Further, the CAF was deposited as ATCC Designation 75559 on Sep. 16, 1993. The invention encompasses any CAF equivalent to and/or substantially equivalent to the deposited CAF as defined by all or any of the above listed characteristics and/or all or any of the characteristics of Table 1.

The term "CAF antibody" shall mean an antibody generated by a mammal with an immune system which antibody binds to and is immunospecific for CAF.

The terms "excipient" and "carrier" are used interchangeably herein to describe any pharmaceutically acceptable and pharmacologically inert ingredients such as sterile water, salts, and buffering agents having a pKa in the physiological range of about 6.0 to about 8.0 and does not include pharmacologically active compounds such as antibiotics, hormones, immunologic stimulators and the like which can be used in combination with CAF to treat patients infected with a retrovirus such as HIV.

The term "lentivirus" is used in its conventional sense to describe a genus of viruses containing reverse transcriptase.

Purified cell factor, CD8$^+$ cell antiviral factor [abbreviated here as CAF] is secreted by peripheral blood mononuclear cells, in particular lymphocytes expressing the molecule defined as CD8 on their cell surfaces. The cells are primarily of the cytotoxic phenotype, CD8+CD11b–CD28+. CAF is obtained from the CD8+ T-cells that have been activated during HIV infection. As indicated above CAF can be precipitated from CD8$^+$ cell supernatant by 53% ammonium sulfate. The CAF of the invention, when purified, has the characteristic (a–p) listed above.

Isolation and Purification

The CAF protein of the invention is purified from conditioned medium in which activated CD8$^+$ cells have been cultured. The CD8$^+$ cells are preferably obtained from an individual carrying HIV yet exhibiting no symptoms associated with HIV-induced disease. The cells are withdrawn in blood by standard venipuncture. The peripheral blood mononuclear cells containing CD8+ lymphocytes are then obtained from the anticoagulant blood buffy coats by gradient centrifugation, e.g., FICOLL/HYPAQUE.

To separate the CD8$^+$ cells from the other peripheral blood mononuclear cells (PMC), a CD8$^+$ specific antibody such as Leu2a (Becton-Dickinson) is used to coat the cells. The CD8$^+$ cells are then captured using support-bound antibodies specific for the antibodies attached to the cells. Column chromatography, magnetic beads, or panning on petri dishes are examples of matrices suitable for such cell separations.

The CD8$^+$ cells are cultured in any suitable cell medium most preferably a RPMI based medium with antibiotics to prevent contamination, interleukin 2 [IL2] and with a mitogenic stimulator (e.g., phytohemagglutinin or anti-T-cell receptor (TCR) coated beads for 2–3 days) to promote secretion of CAF. For purification of the factor, cultivation of CD8$^+$ cells in AIM V (GIBCO) serum-free medium is preferred. It has been observed that the optimal production of CAF by CD8$^+$ cells occurs within 7 to 11 days after the stimulation of those cells with mitogen or anti-CD3 antibodies.

After a suitable incubation (5 to 13 days), the conditioned cell medium is obtained by either microfiltration or differential centrifugation. The cells can be recovered and refed with fresh medium or replaced. The conditioned medium is then subjected to protein purification procedures designed to eliminate contaminating by-products and concentrate the CAF in each step. Heating inactivates contaminating cellular proteins that might be present and then, after removing the precipitate, standard protein purification procedures are used on the fluid such as molecular sizing, immunospecific affinity. Additional chromatographic columns can also be used.

The CAF is purified to a single band on a polyacrylamide gel or HPLC column (about 90% pure). After purification the CAF may be formulated using standard pharmaceutical excipients (e.g., physiological saline). The CAF can be stored in a lyophilized state or frozen in liquid medium at −20°C. or −70°C.

Use and Administration

CAF may be administered by injection into the circulatory system. For example, CAF may be dissolved into sterile water, or other aqueous sterile solutions buffered at physiological range of pH 6.4–8.4. The formulation is preferably made isotonic to blood cells. In addition, the CAF formulation may include other pharmaceutically active ingredients such as antibiotics, antiviral agents, hormones and the like. An injectable CAF formulation will generally contain substantially more excipient (2 to 20 times the amount) than the amount of CAF. The amount of formulation administered in treating a patient will depend on the number of units of CAF in a dose wherein one unit of CAF in the concentration of CAF needed to reduce HIV replication in HIV infected peripheral mononuclear cells by 50% using the assay described herein. The CAF is administered in an amount of about 1,000 to about 10,000 units per kilogram of body weight (human) per day. However, dosing amounts can be adjusted by the caregiver based on factors such as the age, sex, and condition of the patient and, patient responsiveness.

Retrovirus (e.g., lentivirus) replication in mammals such as HIV in humans or feline immunodeficiency virus in cats may be inhibited by the administration of CAF. A typical patient is treated by injecting between 1,000–10,000 units of CAF per kilogram of body weight each day until the patient has recovered clinically and the T-cell count returns to normal.

Assays

The CAF of the invention can be used to produce a variety of different types of useful assay devices. In general, in order to make an assay device the CAF is formulated and injected into a non-human mammal with an immune system such as a goat or mouse using standard protocols for the generation of antibodies. Sufficient time is allowed to pass for the antibodies to be generated and the animal is bled and the antibodies extracted. The extracted antibodies which are immunospecific for CAF can be used within a standard ELISA assay in order to detect the prevalence of CAF within body fluids. Further, by carrying out the assay with respect to a statistically significant segment of the population it is possible to determine normal levels of CAF and thereby determine what abnormally low and high levels of CAF are. As indicated in the above-cited Mackewicz, et al. article the present inventors have noted the relationship between CAF activity and the clinical condition of an individual infected with HIV. In that an ELISA assay produced using antibodies of the present invention could be used to measure CAF levels in the blood the assay could be used to diagnose and thereafter more effectively treat AIDS patients.

Known protocols using specific cell lines and animals (e.g. mice) can be used to produce monoclonal antibodies which are immunospecific for CAF. The monoclonal antibodies can be used to produce an ELISA for detecting CAF in blood and to detect CAF specifically on the surface of lymphocytes. Such assays would be useful as a prognostic indicator, i.e. used to determine which HIV infected individuals might develop AIDS. Particularly low levels of CAF (and/or cells producing CAF) would be likely to show AIDS as a disease with the level being related to the degree the individual is infected with HIV. Labeled monoclonal antibodies are adaptable for use with flow cytometry. Thus labeled monoclonal antibodies are an aspect of the present invention.

Assays including ELISA of the invention can be used for a method of the invention which tests the effectiveness of different treatments. For example, an assay of the invention can be used to test a patient's blood before and during treatment with a given compound. The results of the assays make it possible to determine what effect the treatment is having on the production of CAF by lymphocytes or determine the effect of CAF levels in the blood. Accordingly, this methodology makes it possible to check the effectiveness of various therapies which are directed at increasing CAF production, which has been related to the condition of HIV-infected individuals.

In addition to using assays of the invention to directly test either qualitatively or quantitatively for the presence of CAF in body fluids the assays could be used to test for CAF production of $CD8^+$ cells in vitro or in vivo. Based on the level of production of a given cell it is possible to use an assay to measure the number of anti-HIV $CD8^+$ cells in the blood of an infected individual. Further, flow cytometry can be employed to measure the quantities of CAF producing cells which information would be helpful in determining the prognosis of HIV infected individuals.

In that antibodies which are immunospecific for CAF are used in connection with different types of assays it is often important to label the antibodies. Accordingly, the invention also includes labeled immunospecific CAF antibodies which are attached to a suitable detectable label such as a radioactive label, fluorescent label, or enzyme activated label. Unlabeled antibodies can be attached to a substrate which substrate can be contacted with a body fluid. If the body fluid includes the appropriate CAF antigen the antigen will bind to the antibodies attached to the substrate. Thereafter, labeled antibodies can be brought into contact with the CAF which is attached to the antibodies on the substrate. The labeled antibodies will attach to the CAF and can be detected.

It should be pointed out that when carrying out an assay method of the invention normal protocols are followed. For example, after bringing the antibodies on a substrate into contact with a body fluid the surface is washed in order to remove unbound material. Further, normal protocols involving blocking are generally used prior to contacting the washed surface with labeled antibodies. Assay procedures can be carried out with a statistically significant number of individuals (both healthy and HIV infected) to determine a normal range for CAF levels. Individuals found to have abnormally low levels of CAF can be treated by the administration of CAF contained within a pharmaceutically acceptable formulation which formulation is most preferably an injectable formulation.

To monitor the purity or effectiveness of the CAF, it is useful to assay for inhibition of replication of HIV in $CD4^+$ cells. Cells are either naturally infected (endogenous virus assay) or artificially infected (acute virus infection assay). In the endogenous virus assay, the $CD4^+$ cells are obtained from individuals known to be infected with HIV using immuno-selection techniques, for example immuno-magnetic beads. By this process small polystyrene spheres with iron oxide cores coated with monoclonal antibodies to the CD4 or CD8 cell surface protein (Dynal Corporation) are added to a sample of separated (by FICOLL/HYPAQUE) PMC. After 20–40 minutes of incubation, the CD4⁺ or CD8⁺ cells are removed by a magnetic capture device. The cells are washed and cultured in RPMI-1640 medium supplemented with 10% FBS, 2 mM glutamine, 1% antibiotics (100 units per ml penicillin and 100 µg per ml streptomycin) and 10 percent human IL2 (Electronucleonics, Silver Spring, Md).

Alternatively using the acute virus infection assay, CD4⁺ cells are obtained from uninfected persons and infected with a defined amount of HIV. The cells are then trypsinized to remove input virus and cultured.

In the endogenous virus assay, the CD4⁺ cells are activated using phytohemagglutinin or anti-TCR beads to rapidly divide and produce HIV. Culture fluids containing CAF or purified CAF are added to the virus-infected cells and the culture fluids assayed for viral magnesium-dependent reverse transcriptase activity at three-day intervals as described in Hoffman, et al., *Virology*, 147, 326 (1985). Alternatively, the replication of virus can be monitored by assaying for other virus specific products such as viral protein p24 as described in *J. Immunology*, 144, 2961–2966 (1990).

CAF Inhibits HIV Replication

The data contained within Table 1 demonstrates the effectiveness of CAF as well as a large number of other cytokines to inhibit HIV replication in acutely infected CD4⁺ cells. The first ten cytokines listed in Table 1 were judged to not have an effect on the replication of HIV in acutely infected CD4⁺ cells. This judgment was made because the resulting samples included only slightly more or slightly less HIV after the CD4⁺ cells were exposed to the listed cytokines as compared with control infected CD4 cells which were not contacted with any cytokine. Four of the cytokines were found to actually enhance HIV replication as compared with a control CD4+cells infected with HIV. The last six listed cytokines, which includes CAF, were judged to inhibit HIV replication in acutely infected CD4⁺ cells. This judgment was made in that each of the six samples showed significantly less HIV after the sample was exposed to the indicated cytokine as compared with samples not contacted with any cytokine.

There are five cytokines (other than CAF) listed within Table 1 which have been shown to inhibit HIV replication. The CD8⁺ cell antiviral factor does not bind to antibodies which are specific for any of the five cytokines listed in Table 1 which five have been shown to inhibit HIV replication. This demonstrates that CD8+ antiviral factor inhibits HIV replication and is a factor which is distinct from the factors known to inhibit HIV replication. These data show that CAF is a single, unique and novel cell-excreted factor responsible for antiviral activity and specifically shows that CAF is capable of carrying out antiviral activity with respect to HIV replication in vitro.

The disclosed antiviral factor does not affect the activation or proliferation of CD4⁺ cells. It does inhibit viral replication by interfering with viral RNA transcription to inhibit HIV replication.

The effect of CAF on viral RNA transcription was also demonstrated when the HIV LTR was linked to a luciferase gene in a Jurkat T cell line (IG5). When virus infection occurs in the IG5 line without CAF, luciferase is produced at high levels. When CAF is added to the culture, the luciferase expression is reduced. Cytokines such as TNF-α or interferon do not appear to have this effect on luciferase expression.

In addition to using CAF to treat patients it can be used to inhibit the replication of a retrovirus in cells (in vitro) by exposing the cells to CAF.

EXAMPLES

The following examples are set forth so as to provide those of ordinary skill in the art with a complete disclosure and description of how to extract, purify and identify the CD8⁺ antiviral factor of the invention and to make and use antibodies and assay device using same and are not intended to limit the scope of the invention. Efforts have been made to ensure accuracy with respect to numbers used (e.g., amounts, temperature, molecular weight, etc.), but some experimental errors and deviation should be accounted for. Unless indicated otherwise, parts are parts by weight, molecular weight is weight average molecular weight, temperature is in degrees Centigrade, and pressure is at or near atmospheric.

EXAMPLE 1

(Culturing activated CD8⁺ cells)

CAF is purified from the conditioned medium containing activated CD8⁺ cells. CD8⁺ cells are obtained from the peripheral blood mononuclear cells (PMC) of individuals with HIV infection. PMC are obtained from blood by separation on FICOLL/HYPAQUE gradients. The cells are washed and cultured in RPMI 1640 medium containing 10% fetal bovine serum (FBS), 1% antibiotics, 10% human IL2. Phytohemagglutinin (3 µg/ml, Sigma) is added at the initiation of a five-milliliter cell culture in a 25 cm³ flask and left for 3 days. The cells are permitted to multiply. After 3 days, the cell lines tested multiplied to approximately 6–10×10⁶ cells per milliliter.

Cell cultures of PMC are enriched or depleted of CD8⁺ or CD16+ cells using the panning procedures of Wysocki and Sato *PNAS USA*, 75, 2844 (1978). Briefly, plastic-adherent cells (macrophages) are first removed and then 20×10⁶ to 30×10⁶ of the non-adherent PMC are incubated in 2 ml of phosphate buffered saline (PBS) containing 10 µg per ml of monoclonal antibodies to either Leu-2a or Leu-11b (Becton-Dickinson) for 20 minutes at room temperature. These antibodies recognize epitopes on the CD8 and CD16 antigens, respectively. The cells are then washed twice, resuspended in 4 mls of PBS containing 1% fetal bovine serum and incubated on a capture plastic petri dish coated with antibody for two hours at 4°C.

The capture plates are prepared using biologic grade petri plates coated with the F(Ab')₂ portion of the goat antibody to mouse immunoglobulin IgG (Tago, Burlingame, Calif.). The plates are coated with a capture antibody (10 µg/ml, in .05 moles Tris, pH 9.5) for 40 minutes at room temperature. Excess antibody is washed off the plate with PBS.

To prevent non-specific attachment of PMC, plates are coated with PBS containing 1% FBS prior to use. After incubation, non-adherent cells (that is, the CD8– or CD16– fraction) are washed off the plate with cold PBS, and adherent cells (CD8⁺ or CD16+) are removed from the plate with a forceful jet of PBS. The Leu 11*b* monoclonal antibody procedure is performed, if necessary, to remove NK cells from the CD8⁺ cells. The effectiveness of the procedures described are assessed by flow cytometry, as described in J. A. Levy, et al., *Clin. Immuno. Immunopath.*, 35, 328 (1984).

The CD8$^+$ enriched cells are then cultured in AIM V medium also including 200 µ/ml of recombinant IL-2 and 1% antibiotics (10 µg/ml streptomycin and 100 µg/ml streptomycin). Culture fluids are changed every 2 days. The cells are allowed to multiply for about 3 days and reached a concentration of 6–10×10$^6$ cells per milliliter. The medium is then separated from the CD8$^+$ cells by centrifugation and then passed through a 45 micron Millipore filter. The presence of CAF is monitored using its ability to inhibit HIV replication in susceptible CD4$^+$ cells.

EXAMPLE 2

(Assaying for CAF activity)

To monitor the purity of the CAF, one assays for the relative inhibition of replication of HIV in CD4$^+$ cells using increasingly purified CAF. The cells are obtained from HIV free individuals, washed and cultured in RPMI1640 medium supplemented with 10% FBS, 2 mM glutamine, 1% antibiotics (100 units per ml penicillin and 100 µg/ml streptomycin) and 10% human IL2 (Electronucleonics, Silver Spring, Md.). Phytohemagglutinin (Sigma Company, St. Louis, Missouri) is added (3 µg/ml) at the initiation of the culture. After three days, cells in the chamber are washed and refed with fresh IL-2 containing medium described above. The cells are then inoculated with 100 TCID$_{50}$ (tissue culture infectious doses) of HIV-1. After 1 hour of incubation, the cells are trypsinized to remove input virus. The CAF factor is added and its affect on virus replication monitored every 2–3 days up to 12 days. More specifically, virus replication is assayed for CAF mediated inhibition of HIV replication as measured by magnesium-dependent reverse transcriptase activity as described in Hoffman, et al., *Virology*, 147, 326 (1985) or p24 antigen production. Titration experiments using 50% inhibition of reverse transcriptase activity as a cutoff for effective CAF activity are conducted.

EXAMPLE 3

(Assaying for CAF)

The CD8$^+$ cell antiviral factor can be identified and distinguished from other cell secreted factors by the following physicochemical assays. A 1 ml sample of purified CAF can be exposed to 1 ml of ethyl ether. After 10 minutes of exposure to the ether at 4°C., the ether (polar) fraction is removed and the ether eliminated by evaporation. Under these conditions CAF activity is found in the aqueous solution without any decrease in activity. In that the CAF is completely recovered in the aqueous phase after ether extraction suggest that CAF is lipid-free.

The CD8$^+$ cell antiviral factor is inactivated by certain pH treatments. An aliquot sample of CAF is exposed to a pH in the ranges of 2–8 for 20 hours. Another sample is exposed to a pH range of 10–12 for 20 hours. After exposure of CAF to these pH's the samples are readjusted to the physiological range of pH 7 and tested for the ability to inhibit reverse transcriptase activity in CD4$^+$ cell cultures. The CAF maintained at a pH of 10–12 will no longer inhibit HIV replication. However, the samples held at pH 2–8 maintain their activity.

The CAF can be further identified by its relative insensitivity to high heat. An aqueous sample of CAF is treated for 56° for 30 minutes or at 100°C. for 10 and 30 minutes. The solution is then cooled, precipitate removed, and the fluid retested for anti-HIV activity. Under these conditions full antiviral affects should be present at 56° and only a reduction of 60% should be seen with the treated material at 100°C. for 30 minutes with 90% recovery of activity after 10 minutes.

The CD8$^+$ antiviral factor of the invention also maintained activity when thawed out after being subjected to freezing. In a similar manner the CAF maintained activity after being subjected to lyophilization (freeze-drying) and thereafter rehydrated.

CAF is insensitive to trypsin activity at 37°C. for one hour. Briefly, after exposure to trypsin at 500 µg per ml, soybean trypsin inhibitor is added to the aqueous solution of CAF. CAF is again assayed for its ability to inhibit HIV replication. Under these conditions no loss of activity is seen.

The CD8$^+$ antiviral factor is sensitive to staph V8 protease, but not to protease type XIA (proteinase K).

In order to verify that CD8$^+$ antiviral factor is a protein which is different from several other proteins which inhibit viral replication, CAF was tested against and found not to be inactivated by antibodies for any of TNFα, TNFβ, TGFβ, IL-4, IL-6, IFNα, IFNβ, or IFNγ.

CAF is inactivated by leupeptin (1–10 µg/ml) pefabloc and α2 macroglobulin but not benzamidine. These findings suggest that CAF is a protease such as a serine protease. CAF binds to the surface of a carboxy methylcellulose SEPHADEX cation exchange resin at pH 6.0, indicating a positively charged molecule at pH 6.0.

The CD8$^+$ antiviral factor does not have any direct inactivating activity on virions. When CAF is mixed with a virus such as HIV-1, HIV-2 and SIV neither the virus nor its infectivity are destroyed.

The CD8$^+$ antiviral factor inhibits transcription from the viral long terminal repeat (LTR) in a chloramphenicol acetyl transferase assay. This is an indication of the ability of how CAF can block HIV RNA transcription.

CAF is not any of the commonly known cytokines. Antibodies to alpha, beta or gamma interferon as well as interleukin 4, interleukin 6, tumor necrosis factor and transforming growth factor β will not inhibit in vitro anti-HIV activity. In comparison studies, none of the tested cytokines offered the extent of viral inhibition provided by CAF with the exception of α and β interferon and TNFα. (See Table 1).

CAF is further defined as not affecting the activation or proliferation of CD4$^+$ cells and CAF blocks HIV replication at RNA transcription.

TABLE 1

| CYTOKINE EFFECT ON HIV REPLICATION IN ACUTELY INFECTED CD4$^+$ CELLS | | |
|---|---|---|
| Effect | Cytokine | % Control$^x$ |
| None | IL-1 | 120 |
|  | IL-3 | 110 |

TABLE 1-continued

CYTOKINE EFFECT ON HIV REPLICATION IN ACUTELY INFECTED CD4+ CELLS

| Effect | Cytokine | % Control<sup>x</sup> |
|---|---|---|
| | IL-5 | 100 |
| | IL-6* | 130 |
| | IL-8 | 90 |
| | G-CSF | 80–120 |
| | GM-CSF | 80–120 |
| | IFNγ* | 90 |
| | IL-10 | 90 |
| | IL-12 | 90 |
| Enhances | IL-2 | 140 |
| | IL-7 | >200 |
| | IL-9 | 160 |
| | TNFα* (low concentration) | 110–160 |
| Inhibits | IL-4* | 30–90^ |
| | IFNα* | 0–10 |
| | IFNβ* | 0–10 |
| | TGFβ* | 60–75 |
| | TNFα* (high concentration) | 30–90 |
| | CD8+ cell antiviral factor | 10–40 |

Results with saturating quantities of the cytokines at the time of peak virus replication.
*Antibodies to this cytokine do not block CD8+ cell anti-HIV activity.
^Delays HIV replication by 3–6 days.
xPercent of the HIV replication in peripheral blood mononuclear cells not cultured with the cytokine (i.e. control cells). Thus, the CD8+ cell antiviral factor inhibits HIV replication by 60 to 90% as compared to the replication without CD8+ cell antiviral factor.

Results with saturating quantities of the cytokines at the time of peak virus replication. * Antibodies to this cytokine do not block CD8+ cell anti-HIV activity. ^ Delays HIV replication by 3–6 days. x Percent of the HIV replication in peripheral blood mononuclear cells not cultured with the cytokine (i.e. control cells). Thus, the CD8+ cell antiviral factor inhibits HIV replication by 60 to 90% as compared to the replication without CD8+ cell antiviral factor.

Deposits

A culture of human peripheral blood CD8+ lymphocytes has been deposited with the American Type Culture Collection (ATCC), Rockville, Md., U.S.A. for patent purposes deposit received Sep. 16, 1993 ATCC Designation CRL 11453. The cell culture was deposited under the conditions specified by the Budapest Treaty on the international recognition of the deposit of microorganisms (Budapest Treaty). Further, cell antiviral factor (CAF) as defined in this application has been deposited with the American Type Culture Collection which deposit was received Sep. 16, 1993 ATCC Designation 75559. The deposit was made with a human CD8+ cell culture (AIM-Vbase) to make it possible to replenish the CAF if necessary. An antiviral factor which is equivalent to and/or substantial equivalent to the deposited material is also considered to be within the scope of this invention.

Availability of the deposited material is not to be construed as a license to practice the invention in contravention of the rights granted under the authority of any government in accordance with its patent laws.

The instant invention is shown and described herein at what is considered to be the most practical and preferred embodiments. It is recognized, however, that departures may be made therefrom which are within the scope of the invention and that obvious modifications will occur to one skilled in the art upon reading this disclosure.

What is claims is:

1. A substantially pure composition of CD8+ cell antiviral factor defined by the following characteristics:

(i) blocks viral replication by inhibiting viral RNA transcription;

(ii) does not affect CD4+ cell activation or proliferation;

(iii) is not a cytokine selected from the group consisting of IL-1, IL-2, IL-3, IL-4, IL-5, IL-6, IL-7, IL-8, IL-9, IL-10, IL-12, G-CSF, GM-CSF, TNFα, TNFβ, IFNα, IFNβ, IFNγ, and TGFβ;

(iv) precipitated from CD8+ cell supernatant by 53% ammonium sulfate; and (v) binds to a carboxy methylcellulose ion exchange resin at pH 6.0;

wherein substantially pure indicates that any of the cytokines of (iii) present in CD8+ cell extract have been separated away.

2. A substantially pure composition of CD8+ cell antiviral factor which is defined by the following properties:

(a) released from activated CD8+ cells;

(b) biologically inactivated when exposed to a pH in a range of 10–12 while maintaining biological activity when exposed to a pH in the range of 2–8;

(c) resistant to heat of 100°C. for 30 minutes to the extent that about 60% of its activity is maintained;

(d) resistant to trypsin;

(e) does not affect CD4+ cell activation or proliferation;

(f) blocks viral replication by inhibiting viral RNA transcription;

(g) function not inhibited by antibodies specific for IFNα, IFNβ, IFNγ, TNFα, TNFβ, TGFβ, IL-6 or IL-4;

(h) is not a cytokine selected from the group consisting of IL-1, IL-2, IL-3, IL-4, IL-5, IL-6, IL-7, IL-8, IL-9, IL-10, IL-12, G-CSF, GM-CSF, TNFα, TNFβ, IFNα, IFNβ, IFNγ, and TGFβ;

(i) activity is maintained after being subjected to freezing and thawing;

(j) sensitive to staph V8 protease but not to protease type XIA (proteinase K);

(k) does not induce 2'-5'-A synthetase in CD4+ lymphocytes and is, accordingly, different from interferon;

(l) precipitated from CD8+ cell supernatant by 53% ammonium sulfate; and (m) lipid free;

wherein substantially pure indicates that any of the cytokines of (h) present in CD8+ cell extract have been separated away.

3. The composition of claim 2, further defined by:

(n) reduces luciferase expression in IG5 cell infected with HIV;

(o) inactivated by leupeptin but not inactivated by benzamidine; and (p) binds to a carboxy methylcellulose ion exchange resin at pH 6.0.

4. The composition of claim 1, which is deposited as ATCC Designation 75559.

5. The composition of claim 1, which composition is obtained from deposited human CD8+ cell culture designation CRL 11453.

6. The composition of claim 2, which is deposited as ATCC Designation 75559.

7. The composition of claim 2, which composition is obtained from deposited human $CD8^+$ cell culture Designation CRL 11453.

8. The composition of claim 1 which is further characterized by having resistance to heat such that when maintained at 100°C. for 10 minutes activity of the composition up to 90% is maintained.

9. The composition of claim 2, wherein the resistance to trypsin is characterized such that the composition is insensitive to trypsin activity at 37°C. for one hour.

* * * * *